United States Patent [19]

Kotsuka

[11] Patent Number: 5,232,433
[45] Date of Patent: Aug. 3, 1993

[54] HYPERTHERMIA DEVICE

[75] Inventor: Youji Kotsuka, Kanagawa, Japan

[73] Assignees: The Tokai University Juridical Foundation, Tokyo; Omron Corporation, Kyoto, both of Japan

[21] Appl. No.: 716,806

[22] Filed: Jun. 19, 1991

[30] Foreign Application Priority Data

Sep. 10, 1990 [JP] Japan ............................. 2-95023[U]
Dec. 19, 1990 [JP] Japan ............................. 2-403927

[51] Int. Cl.[5] ............................................. A61N 2/00
[52] U.S. Cl. ............................................ 600/10; 600/9
[58] Field of Search ...................................... 600/9–15; 128/419 F

[56] References Cited

U.S. PATENT DOCUMENTS 4,454,883  6/1984  Fellus.
4,587,978  5/1986  Suyama et al.
5,090,423  2/1992  Matsuda et al. ...................... 600/14

FOREIGN PATENT DOCUMENTS 0208338  1/1987  European Pat. Off.
3324119  1/1985  Fed. Rep. of Germany .......... 600/9
2210420  7/1974  France.
8903706  5/1989  PCT Int'l Appl.
275614   5/1951  Switzerland.

OTHER PUBLICATIONS

IEEE Transactions on Magnetics, vol. 23, No. 5, Sep. 1987, 2437–2439, S. Ueno et al., "Localized hyperthermia by means of paired–coil configuration: calcluation of current distributions in cubical model".

*Primary Examiner*—Lee S. Cohen
*Assistant Examiner*—John P. Lacyk
*Attorney, Agent, or Firm*—Fish & Richardson

[57] ABSTRACT

A hyperthermia device includes a pair of magnetic poles for applying an alternating magnetic field in a body to be heated, these two magnetic poles being laterally arranged on the surface of the body and having time varying polarities opposite to each other, and allowing a line of magnetic force including a component perpendicular to the surface of the body in the vicinity of these magnetic poles.

13 Claims, 7 Drawing Sheets

HYPERTHERMIA DEVICE

BACKGROUND OF THE INVENTION

1. Field of the Invention

The present invention relates generally to hyperthermia devices, and more particularly, to hyperthermia devices utilizing induction heating.

2. Description of the Background Art

Solenoids have been commonly used as magnetic applicators for induction heating in hyperthermia. A magnetic applicator comprising a magnetic core such as ferrite and a coil winding around the same is particularly preferable to a magnetic applicator including only a solenoid in that it is capable of locally concentrating electric field. In induction heating in general, however, eddy current density tends to be high in a peripheral portion of a body to be heated and it is therefore difficult to selectively heat a desired local region in the body. In particular, it is difficult to heat a portion located deep in the body.

FIG. 1A located schematically shows a main portion of a conventional hyperthermia device and FIG. 1B shows a section taken along the chain dotted line of FIG. 1A. The hyperthermia device comprises a pair of magnetic applicators 1a and 1b arranged to have a body 4 to be heated provided therebetween. The magnetic applicators 1a and 1b include magnetic cores 2a and 2b, and coils 3a and 3b, respectively. An alternating field is applied to the body 4 by a flow of the alternating currents of the same phase to the coils 3a and 3b of the magnetic applicators 1a and 1b, respectively. The alternating field generates an eddy current in the body 4 which will be heated by Joule heat generated by the eddy current.

The hyperthermia device shown in FIG. 1A is designed to have the central portion of the body 4 through which the common axis of the magnetic cores 2a and 2b, that is, the central portion of the section 4a of FIG. 1B heated. As described above, however, the eddy current density tends to be high in the peripheral portion of the body 4 and consequently, there is a tendency that only the peripheral portion of the section 4a is heated while the central portion of the same is not heated. Then, as shown in FIG. 1B, hot spots 4b might be produced in the peripheral portion of the body 4.

FIG. 2A shows the distribution of eddy current densities in the section 4a obtained as a result of simulation performed by the finite element method using, phantom equivalent to muscle as the body 4 shown in FIG. 1A. The phantom 4 has an electric conductivity of 0.62S/m and a dimension of $30 \times 30 \times 30$ cm$^3$. An alternating field having a frequency of 5 MHz is applied to the phantom 4 and the line of magnetic force runs perpendicular to the surface of the drawing FIG. 2A. Each vector shown in the phantom 4 has a length proportional to an eddy current density and the vector shown at the lower right of FIG. 2A corresponds to an eddy current density of 1.2 kA/m$^2$. It is clear from FIG. 2A that the eddy current density is high in the peripheral portion of the phantom 4, in particular, in the regions corresponding to the hot spots 4b shown in FIG. 1B. In the drawing, the axis x represents a horizontal position of the phantom 4 and the axis y represents a vertical position thereof.

FIG. 2B shows electric power loss at positions along the line 2B—2B of FIG. 2A. The line 2B—2B crosses the phantom 4 at a height of y=15 cm in a direction along the axis x. The electric power loss is electric energy consumed for generating the Joule heat, and the larger the electric power loss of a position is, the more the temperature of the position increases. As is clear also from FIG. 2B, the central portion of the section 4a of the phantom 4 is barely heated as compared with the peripheral portion thereof.

As described above, the prior art hyperthermia device has difficulty in selectively heating a desired local region of a body to be heated, in particular, to heat a portion located deep in the body.

SUMMARY OF THE INVENTION

In view of the prior art, an object of the present invention is to provide a hyperthermia device capable of selectively heating a desired local region of a body to be heated, and in particular, a region located deep in the body.

The hyperthermia device according to the present invention includes a pair of magnetic poles for applying an alternating field in a body to be heated, these two magnetic poles being a lateral arranged on the surface of the body and having time varying polarities opposite to each other, the line of magnetic force including a component be perpendicular to the surface of the body in the vicinity of these magnetic poles.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 3A:
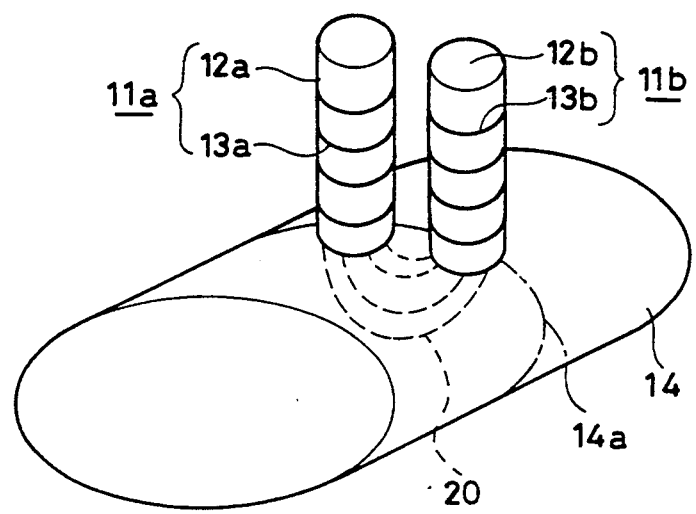
FIG. 3A is a schematic perspective view showing the main portion of a hyperthermia device according to a first embodiment of the present invention.
Figure 3B:
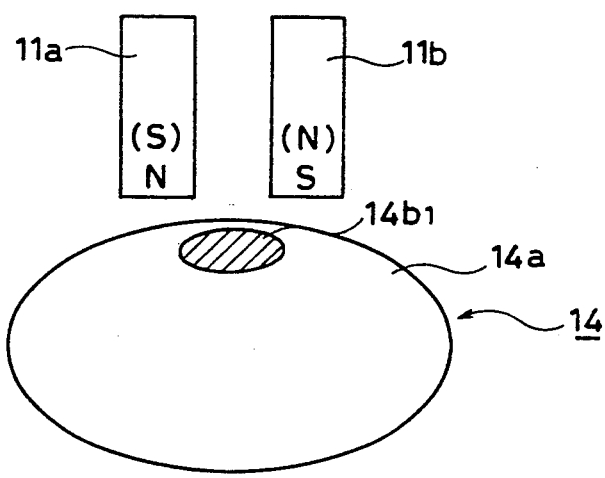
FIG. 3B is a sectional view of the body to be heated shown in FIG. 3A.

FIG. 3A is a schematic perspective view of the main portion of a hyperthermia device according to a first embodiment of the present invention and FIG. 3B shows a section taken along the chain dotted line of FIG. 3A. The hyperthermia device comprises a pair of magnetic applicators 11a and 11b for applying an alternating magnetic field in a body 14 to be heated having an oval section similar to that of a human body. These two magnetic applicators 11a and 11b include magnetic cores 12a and 12b, and coils 13a and 13b wound around the same, respectively. The magnetic cores 12a and 12b are preferably hollow and supplied with such cooling medium as water.

The two magnetic applicators 11a and 11b are laterally arranged on the surface of the body 14, such that magnetic coupling is generated between the two magnetic poles on the surface of the body 14 as indicated by the broken line 20 in FIG. 3A. In other words, the alternating currents are applied to the coils 13a and 13b, with phases allowing the two magnetic poles on the surface of the body 14 to have time varying polarities opposite to each other (see the time varying magnetic polarities N and S shown in FIG. 3B).

The magnetic cores 12a and 12b provided spaced from each other in the drawing can be replaced by one magnetic core of inverted U shape, for example.

Figure 1A:
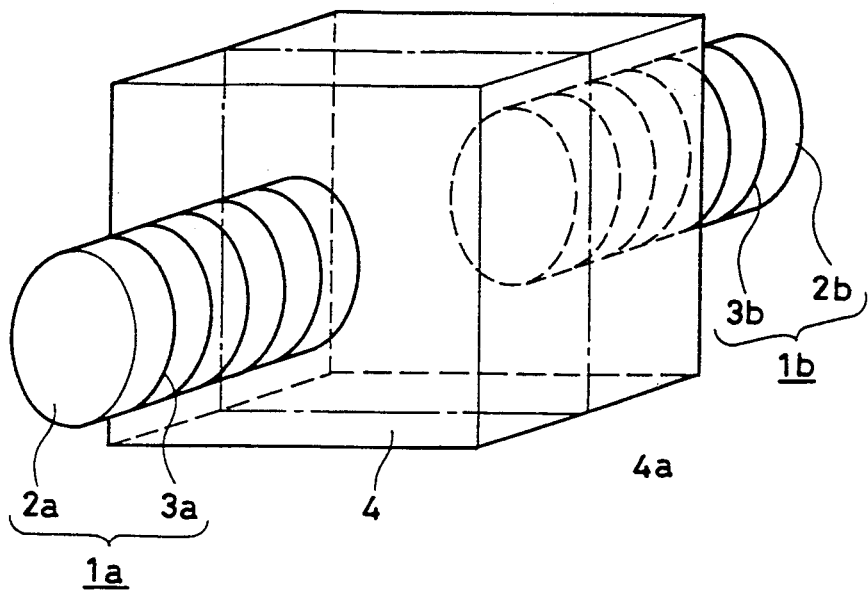
FIG. 1A is a schematic perspective view showing a main portion of a prior art hyperthermia device.
Figure 1B:
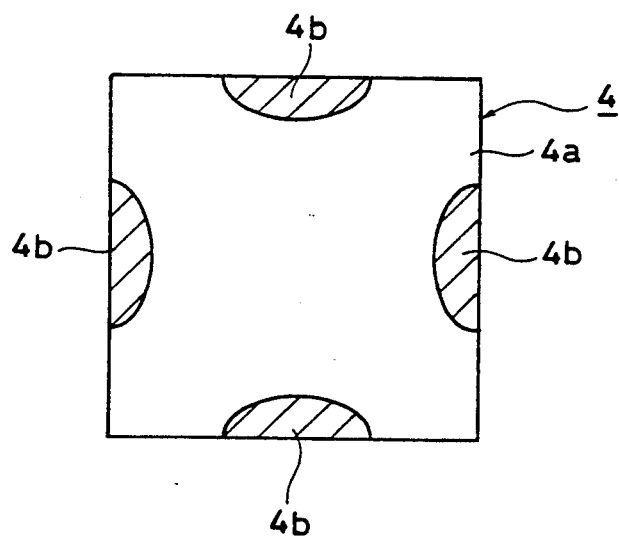
FIG. 1B is a sectional view of a body to be heated shown in FIG. 1A.
Figure 2A:
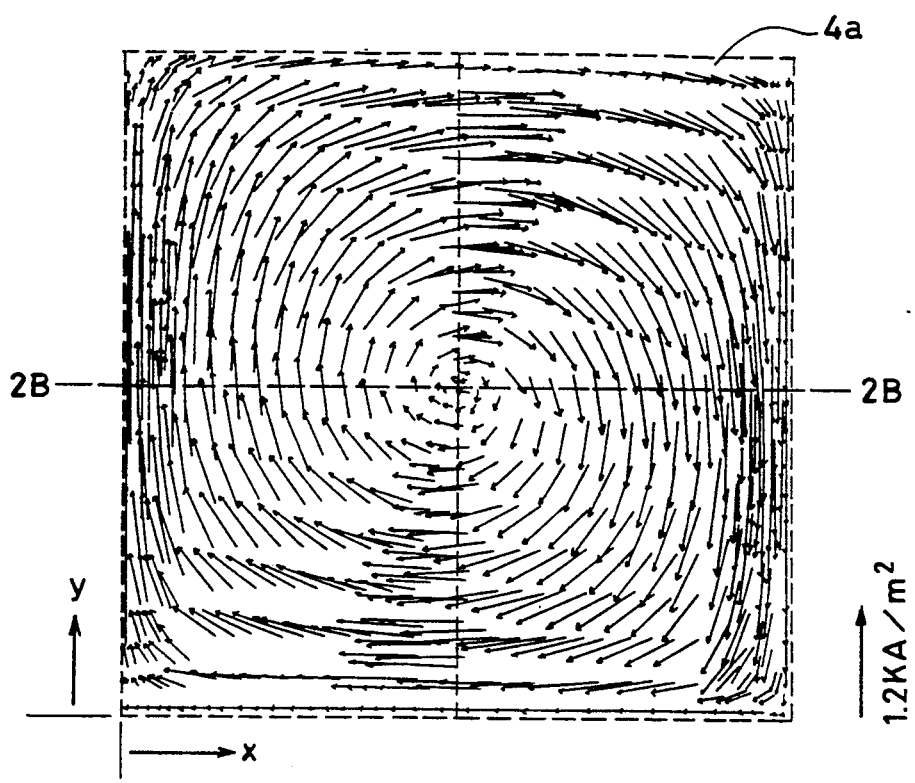
FIG. 2A is a diagram showing the distribution of eddy current densities in the section shown in FIG. 1B.
Figure 2B:
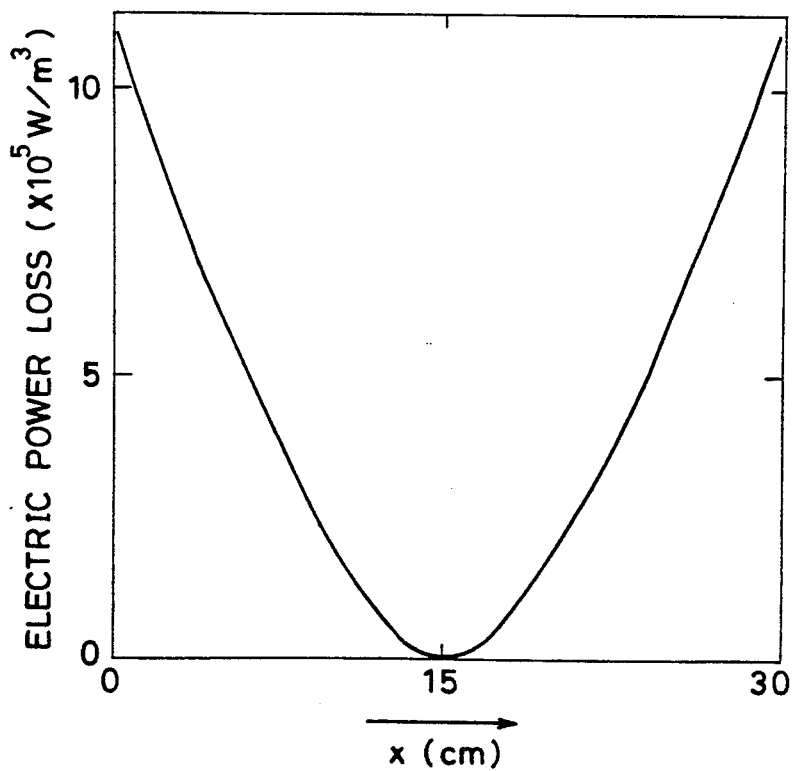
FIG. 2B is a graph showing electric power loss at positions along the line 2B—2B of FIG. 2A.

FIG. 3B shows an actually heated region 14b1 in a section 14a of the body 14 to be heated. The heated region 14b1 exists in the vicinity of the surface layer of the body 14. While the prior art hyperthermia device shown in FIG. 1A has difficulty in selectively heating a desired region near the surface layer of the body 4, the hyperthermia device according to the first embodiment shown in FIG. 3B is capable of selectively heating a desired region near the surface layer of the body 14 with ease without producing undesired hot spots in the other regions. The reason for this is that only the region near the magnetic polarities of the magnetic applicators 11a and 11b is heated in the first embodiment, as can be seen from FIG. 3B.

Figure 4A:
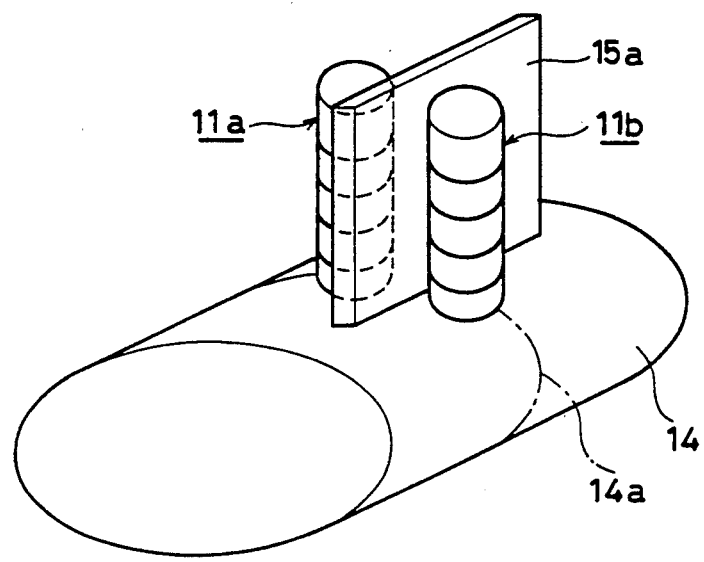
FIG. 4A is a schematic perspective view showing a hyperthermia device according to a second embodiment of the present invention.
Figure 4B:
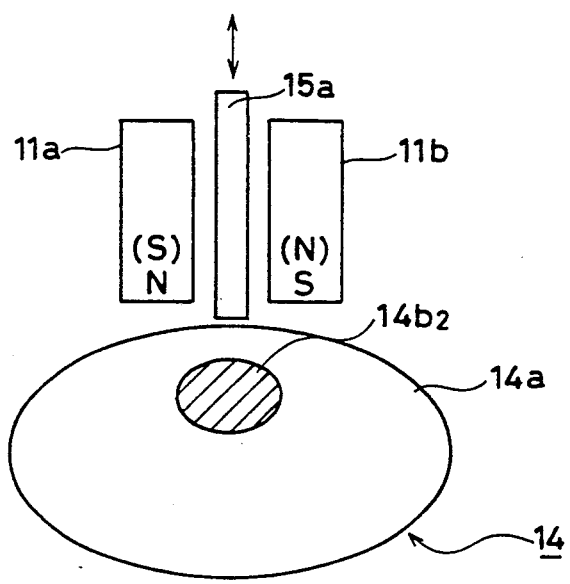
FIG. 4B is a sectional view of the body to be heated shown in FIG. 4A.

FIG. 4A is a perspective view of the main portion of a hyperthermia device according to a second embodiment of the present invention and FIG. 4B shows a section taken along the chain dotted line of FIG. 4A. The hyperthermia device according to the second embodiment similar to that according to the first embodiment further comprises a plate 15a showing diamagnetic nature, for example, as magnetic field controlling means provided between the magnetic applicators 11a and 11b. A metal plate (e.g., copper, aluminum, etc.) having a high electric conductivity can be used for the plate 15a showing diamagnetic nature. In particular, bismuth and lead showing strong diamagnetism nature may preferably be used for the plate 15a.

As indicated by the bidirectional arrow in FIG. 4B, the diamagnetic plate 15a is movable between the magnetic applicators 11a and 11b to come near to the body 14 and away from the same. Adjustment of the position of the diamagnetic plate 15a on the surface of the body 14 controls the distribution of lines of magnetic force generated from the magnetic applicators 11a and 11b.

As the diamagnetic plate 15a comes nearer to the body 14, the component of the line of magnetic force perpendicular to the surface of the body is increased. That is, when the diamagnetic plate 15a is located near the body 14, the line of magnetic force penetrates deep in the body 14 to enable heating of a region 14b2 deeper in the body. In other words, a depth of the region 14b2 to be heated can be controlled by adjusting the position of the diamagnetic plate 15a.

Figure 5:
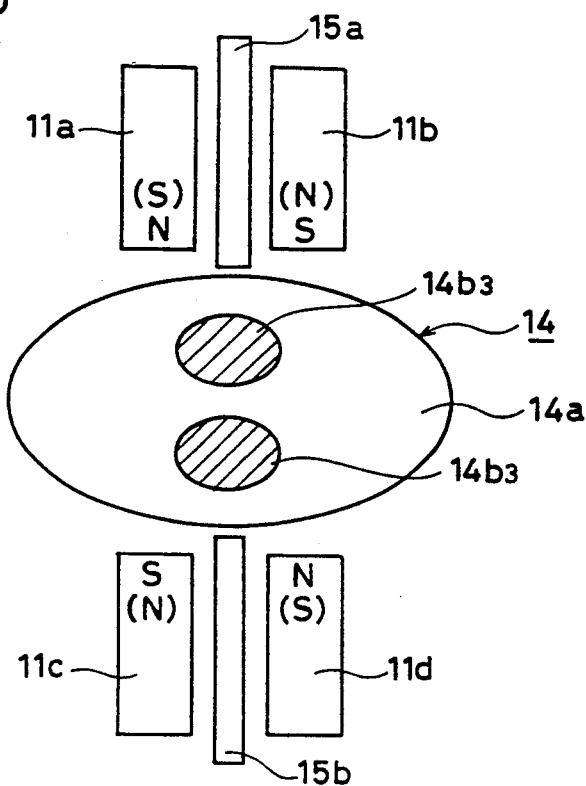
FIG. 5 is a sectional view showing a third embodiment of the present invention.

FIG. 5 schematically shows a third embodiment of the present invention. The hyperthermia device of FIG. 5 similar to that of FIG. 4B further comprises a second pair of magnetic applicators 11c and 11d and a second diamagnetic plate 15b provided therebetween. The first pair of magnetic applicators 11a and 11b and the second pair of magnetic applicators 11c and 11d are provided to have the body 14 provided therebetween. The magnetic poles of the magnetic applicators 11a and 11c arranged opposite to each other have time varying polarities opposite to each other and similarly, the magnetic polarities of the magnetic applicators 11b and 11d provided opposite to each other have time varying polarities opposite to each other. FIG. 5 shows that two regions 14b3 relatively deep in the body 14 are heated with the diamagnetic plates 15a and 15b located near the body. In a case of a relatively thin body 14 to be heated, the two regions 14b3 to be heated turn out to be one region, which means that the central portion located deepest in the body 14 is heated.

Figure 6:
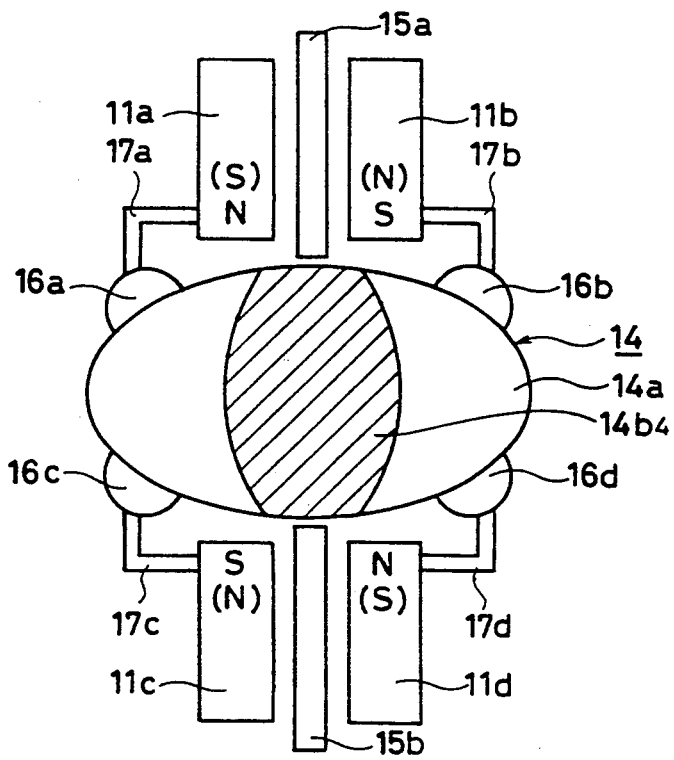
FIG. 6 is a sectional view showing a fourth embodiment of the present invention.
Figure 7:
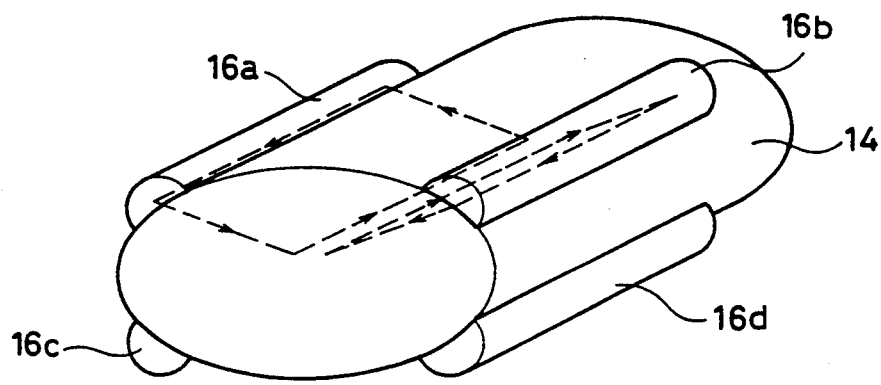
FIG. 7 is a perspective view showing an eddy current loop in auxiliary electrodes and a body to be heated shown in FIG. 6.

FIG. 6 schematically shows a fourth embodiment of te present invention. The hyperthermia device of FIG. 6 similar to that of FIG. 5 further comprises four auxiliary electrodes 16a-16d provided on and in contact with the surface of the body 14 to be heated. The perspective view of FIG. 7 more clearly shows the auxiliary electrodes 16a-16d. The auxiliary electrodes 16a-16d can be formed by a metal material or a conductive rubber material including metal powder. The auxiliary electrodes 16a-16d are preferably hollow and supplied with such cooling medium as water, for example. Furthermore, the auxiliary electrodes 16a-16d may be attached to the corresponding magnetic applicators 11a-11d by means of the corresponding insulating arms 17a-17d, respectively, as shown in FIG. 6.

The auxiliary electrodes 16a-16d function to absorb the eddy current near the surface of the body 14 to prevent formation of undesired hot spots near the surface layer. In addition, the auxiliary electrodes 16a-16d facilitates a formation of an eddy current loop as shown by the dotted line loop in FIG. 7, thereby enabling generation of an eddy current and improving the heat efficiency at the central portion located deepest in the body 14. Like to the diamagnetic plates 15a and 15b, the auxiliary electrodes 16a and 16d arranged as shown in FIG. 6 function to increase the component of the line of magnetic force perpendicular to the surface of the body 14, thereby further facilitating the penetration of the line of magnetic force to a portion deepest in the body. Therefore, the hyperthermia device of FIG. 6 allows the central portion 14a to be reliably heated without producing undesired hot spots at the surface layer of the body 14.

Figure 8A:
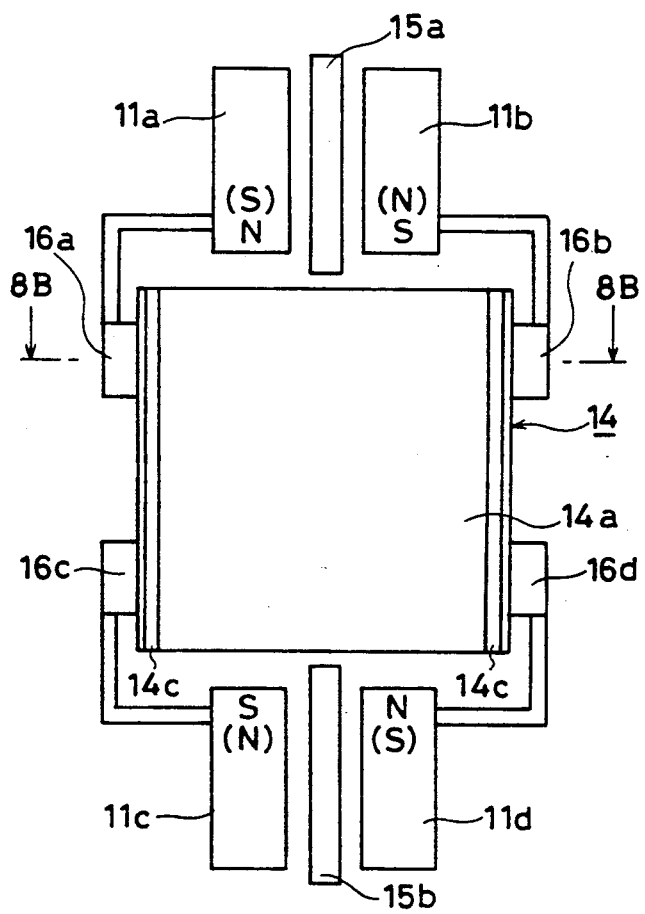
FIG. 8A is a sectional view showing a hyperthermia device and a body to be heated for use in simulation for examining eddy current densities in a body according to the fourth embodiment of the present invention.
Figure 8B:
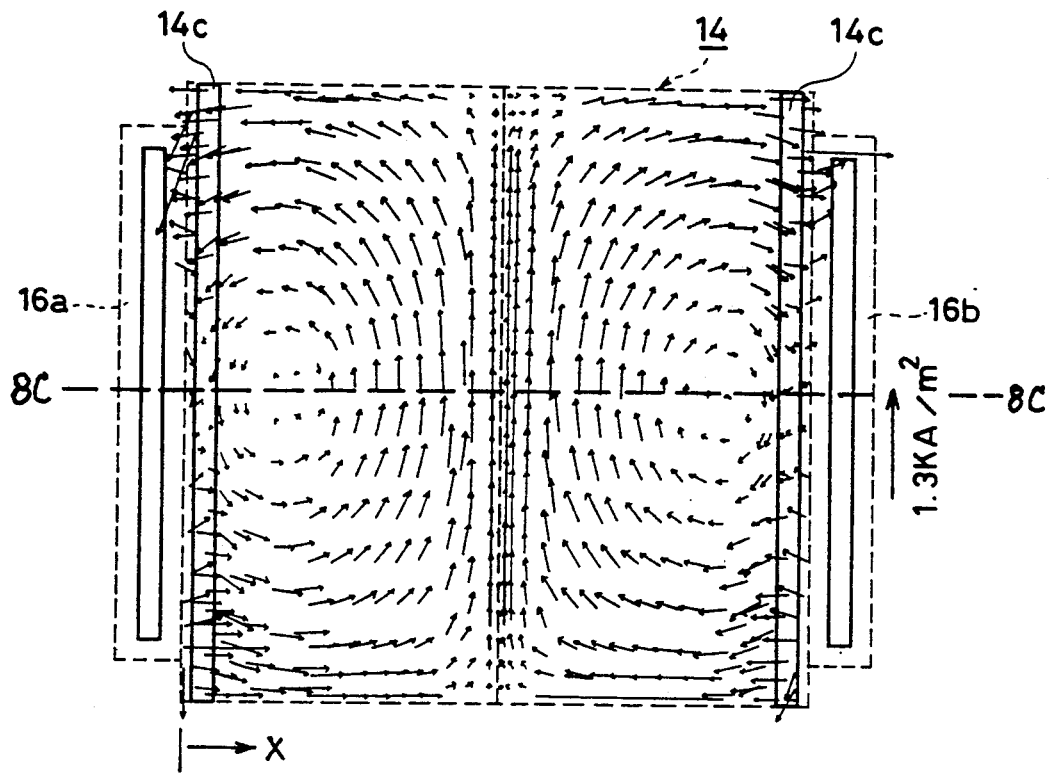
FIG. 8B is a diagram showing the distribution of eddy current densities in the section taken along the line 8B—8B of FIG. 8A.

FIG. 8A shows simulation for examining heating characteristics of a hyperthermia device according to the fourth embodiment. Phantom 14 of $30 \times 30 \times 30$ cm$^3$ is used in this simulation. The phantom 14 has fat layers of 1.0 cm thickness with an electric conductivity of 0.047S/m at positions inside by 0.5 cm from the right and left side surface and then the remaining portion formed by muscle with an electric conductivity of 0.62S/m. The alternating current of 4 MHz is applied to the magnetic applicators 11a-11d. The auxiliary electrodes 16a-16d are provided on and in contact with the right and the left side surfaces of the phantom 14 and formed by conductive rubber having an electric conductivity of $2.0 \times 10^4$ S/m. In addition, the auxiliary electrodes 16a-16d are formed to be hollowed and supplied with cooling water having an electric conductivity of $1.0 \times 10^{-3}$ S/m. FIG. 8B shows one example of the results of such simulation as shown in FIG. 8A.

FIG. 8B shows the distribution of eddy current densities at the section taken along the line 8B—8B of FIG. 8A. The vector shown along the auxiliary electrode 16b at the right side has a length corresponding to a current density of 1.3 kA/cm². It is understood from the section of the phantom shown in FIG. 8B that the current density is high at the central portion at which two eddy current loops come in contact with each other. In other words, the central portion of the section is heated most.

Figure 8C:
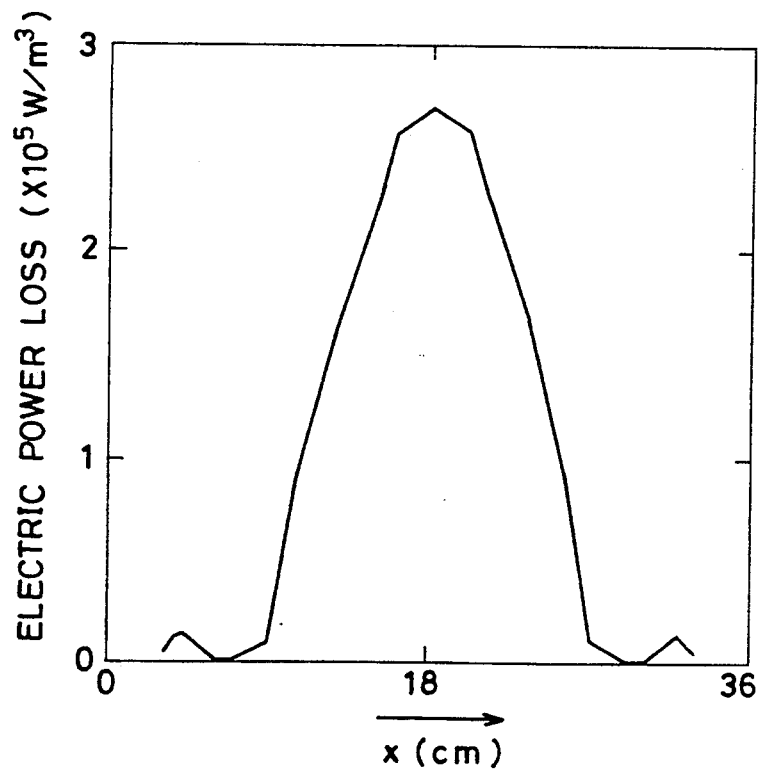
FIG. 8C is a graph showing electric power loss at positions along the line 8C—8C of FIG. 8B.

FIG. 8C shows electric power loss at positions along the line 8C—8C of FIG. 8B. The line 8C—8C crosses the phantom 14 in a direction along the axis x. As is clear from 8C, the electric power loss is small in the vicinity of the surface layer of the phantom 14 and it is large at the central portion. That is, it can be understood that the hyperthermia device according to the fourth embodiment allows the central portion located deepest in the body 14 to be reliably heated without producing undesired hot spots in the vicinity of the surface of the body 14.

Although the present invention has been described and illustrated in detail, it is clearly understood that the same is by way of illustration and example only and is not to be taken by way of limitation, the spirit and scope of the present invention being limited only by the terms of the appended claims.

I claim:

1. A hyperthermia device comprising:
   a first pair of magnetic pole means for applying an alternating magnetic field to induce heat in a body,
   said first pair of magnetic pole means adapted to be arranged perpendicular to a surface of said body, parallel to each other and spaced from each other laterally above the surface of said body proximate to the region of said body to be heated, and
   said first pair of magnetic pole means having time varying magnetic polarities opposite to each other and producing lines of magnetic force of said alternating magnetic field including a component perpendicular to the surface of said body in the vicinity of said first pair of magnetic pole means.

2. The hyperthermia device according to claim 1, further comprising magnetism controlling means provided between said two magnetic pole means for controlling the distribution of the lines of magnetic force produced from said two magnetic pole means.

3. The hyperthermia device according to claim 2, wherein said magnetism controlling means increases the component of said line of magnetic force perpendicular to the surface of said body.

4. The hyperthermia device according to claim 2, wherein said magnetism controlling means includes a diamagnetic plate inserted between said two magnetic pole means.

5. The hyperthermia device according to claim 4, wherein said diamagnetic plate includes a metal plate having a high electric conductivity.

6. The hyperthermia device according to claim 4, wherein said diamagnetic plate includes a bismuth plate.

7. The hyperthermia device according to claim 4, including means for moving said diamagnetic plate between said two magnetic pole means to come near to and away from said body.

8. The hyperthermia device according to claim 2, further comprising a second pair of magnetic pole means similar to said first pair of magnetic pole means, wherein said first and second pairs of magnetic pole means are adapted to be arranged with the body provided therebetween.

9. The hyperthermia device according to claim 8, wherein a time varying polarity of one magnetic pole means of said first pair is at any time set to be opposite to a time varying polarity of one magnetic pole means of said second pair which means is arranged opposite to said means of first pair.

10. The hyperthermia device according to claim 8, further comprising a plurality of auxiliary electrode means for contacting the surface of said body, wherein said auxiliary electrode means function as a part of a closed loop of an eddy current formed in said body, thereby preventing generation of undesired hot spots in the vicinity of the surface of said body while effectively heating a portion located deepest in the body.

11. The hyperthermia device according to claim 10, including means for supplying said auxiliary electrode means with cooling medium.

12. The hyperthermia device according to claim 10, wherein said auxiliary electrode means also function to increase the component of said line of magnetic force perpendicular to the surface of said body.

13. The hyperthermia device according to claim 10, including means for supplying said magnetic pole means with cooling medium.

* * * * *